United States Patent [19]

Langberg

[11] Patent Number: 5,370,644

[45] Date of Patent: Dec. 6, 1994

[54] RADIOFREQUENCY ABLATION CATHETER

[75] Inventor: Edwin Langberg, Mount Laurel, N.J.

[73] Assignee: Sensor Electronics, Inc., Mount Laurel, N.J.

[21] Appl. No.: 93,177

[22] Filed: Jul. 16, 1993

Related U.S. Application Data

[60] Division of Ser. No. 819,597, Jan. 9, 1992, Pat. No. 5,246,438, which is a continuation of Ser. No. 435,361, Nov. 17, 1989, abandoned, which is a continuation-in-part of Ser. No. 276,294, Nov. 25, 1988, Pat. No. 4,945,912.

[51] Int. Cl.$^5$ .............................. A61N 5/00; A61B 5/04
[52] U.S. Cl. .................................. 606/33; 128/642; 607/101; 607/113; 607/122; 607/156
[58] Field of Search ............... 128/642; 606/33, 41; 600/12; 607/101, 102, 113, 122, 154, 156

[56] References Cited

U.S. PATENT DOCUMENTS

| | | |
|---|---|---|
| 4,074,718 | 2/1978 | Morrison, Jr. . |
| 4,154,246 | 5/1979 | LeVeen . |
| 4,352,360 | 10/1982 | King . |
| 4,583,556 | 4/1986 | Hines et al. . |
| 4,641,649 | 2/1987 | Walinsky et al. . |
| 4,658,836 | 4/1987 | Turner . |
| 4,700,716 | 10/1987 | Kasevich et al. . |
| 4,754,752 | 7/1988 | Ginsburg et al. . |
| 4,785,815 | 11/1988 | Cohen . |
| 4,825,880 | 5/1989 | Stauffer et al. . |
| 4,841,988 | 6/1989 | Fetter et al. . |
| 4,896,671 | 1/1990 | Cunningham et al. . |
| 4,945,912 | 8/1990 | Langberg . |
| 5,057,106 | 10/1991 | Kasevich et al. ............ 606/33 |

FOREIGN PATENT DOCUMENTS

| | | |
|---|---|---|
| 0182689 | 5/1986 | European Pat. Off. . |
| 249631 | 9/1987 | German Dem. Rep. . |
| 2822829 | 11/1979 | Germany . |
| 2122092 | 1/1984 | United Kingdom . |
| 1266548 | 10/1986 | U.S.S.R. . |

OTHER PUBLICATIONS

"Tissue Heating During Radiofrequency Catheter Ablation: A Thermodynamic Model and Observations in Isolated Perfused and Superfused Canine Right Ventricular Free Wall", Jun. 1989 *PACE*.
"Catheter Ablation Without Fulguration: Design & Performance of a New System", 1989.
Lyons et al., "Localized Hyperthermic . . . Array", IEEE Trans. Biomed. Eng., vol. 31, No. 1, pp. 53–54 Jan., 1984.
Lin et al., "An Implantable . . . Hyperthermic", Proc. of the IEEE, vol. 75, No. 8, pp. 1132–1133, Aug. 1987.
Ryan et al., "Variations in the Design . . . Hyperthermia", Proc. 14th Annual NE Bio. Conf. IEEE, Mar. 1988, pp. 130–132.
Satoh et al., "Implantable Helical Coil Microwave Antenna . . . ", Int. J. Hyperthermia, vol. 4, No. 5, 1988, pp. 497–572.

*Primary Examiner*—Lee S. Cohen
*Attorney, Agent, or Firm*—Ryan, Kees & Hohenfeldt

[57] ABSTRACT

A cardiac ablation apparatus including a solenoidal antenna, monitoring electrodes, and a coupling network at a distal end of a catheter transmission line, and another coupling network at the proximal end of the catheter transmission line to connect the catheter to the source of radiofrequency (RF) power and to an intracardiac electrogram monitor. Solenoidal antenna design includes single and multiple windings with varying geometrical features. Plated plastic tri-axial design of a transmission line offers unitary fabrication. A catheter with variable impedance electrode and gap coatings has features useful for both ablation and for hyperthermia applications.

12 Claims, 4 Drawing Sheets

RADIOFREQUENCY ABLATION CATHETER

This is a continuation of copending application Ser. No. 07/819,597 filed Jan. 9, 1992, now U.S. Pat. No. 5,246,438, which is a continuation of Ser. No. 07/435,361 filed Nov. 17, 1989 (abandoned), which is a continuation-in-part of Ser. No. 07/276,294 filed Nov. 25, 1988, (now U.S. Pat. No. 4,945,912 dated Aug. 7, 1990).

FIELD OF THE INVENTION

This invention pertains to a catheter designed to couple radiofrequency (RF) energy to biological tissue surrounding the catheter tip. Typical application is in thermal ablation of cardiac tissue. This invention further pertains to an apparatus used to guide a cardiac ablation catheter to ablate arrhythmia-causing myocardial tissue and to monitor the ablation procedure by detecting, processing, and displaying endocardial EKG signals.

BACKGROUND OF THE INVENTION

Percutaneous thermal destruction (ablation) of problem myocardial tissue (arrhythmogenic focus) is a therapeutic procedure used with increasing frequency for treatment of cardiac arrhythmias (e.g., ventricular tachycardia).

Medically, ablation is covered in *Ablation in Cardiac Arrhythmias*, G. Fontaine & M. M. Scheinman (Eds.), Futura Publishing Company, New York, 1987. A recent review of the ablation field is given in a chapter by D. Newman, G. T. Evans, Jr., and M. M. Scheinman entitled "Catheter Ablation of Cardiac Arrhythmias" in the 1989 issue of *Current Problems in Cardiology*, Year Book Medical Publishers.

Catheter ablation of ventricular tachycardia was first described in 1983 as a nonsurgical method of destroying an arrhythmogenic focus. Typically, a pacing catheter is introduced percutaneously and advanced under fluoroscopic guidance into the left heart ventricle. It is manipulated until the site of earliest activation during ventricular tachycardia is found, indicating the location of problem tissue. One or more high voltage direct-current pulses from a standard defibrillator are then applied between the distal electrode of the catheter and an external large-diameter chest wall electrode. This procedure works by destroying cardiac tissue responsible for the arrhythmia.

Although this treatment is effective in some patients, there are serious drawbacks to high voltage direct-current pulses as an ablative energy source. The shock is painful, so general anesthesia is required. More importantly, the discharge produces arcing and explosive gas formation at the catheter tip. The resultant shock wave is responsible for serious side effects. The scar created by a direct-current pulse tends to have a large border zone of injured but still viable tissue that may serve as a new focus for ventricular tachycardia.

These problems have prompted a search for alternatives to direct-current pulse as a source of ablative energy. Radiofrequency (RF) energy is a promising method being investigated. (RF without qualifiers refers here to the electromagnetic spectrum from 10 kHz to 100 GHz, as per ANSI/IEEE Standard 100-1988.) Laser energy is also being considered for catheter ablation of arrhythmias (see Cohen, U.S. Pat. No. 4,685,815) but is not pertinent to the RF implementation considered here.

RF ablation using electrosurgical power units is in clinical investigation, as a safer ablation alternative to high voltage direct current pulses. At present, continuous, unmodulated current in the range of 0.5 MHz to 1.2 MHz, such as that supplied by an electrosurgical RF power supply, is applied to the endocardium via an electrode catheter in the same manner as with a direct-current pulse. Ablative injury is produced by heating, generated by an electric field emanating from the catheter electrode. There is no gas or shock wave formation, and therefore no risk of serious barotraumatic side effects. However, as discussed in more detail later, the small size of the resulting lesion remains a problem even with RF ablation.

In order to discuss and evaluate the technical state of the art of RF ablation catheters and to compare it with embodiments of this invention, one must first establish pertinent performance requirements. A general geometrical requirement of catheter-based applicators is that they must be confined in a slender cylindrical structure with a radius commensurate with the catheter diameter. Subcutaneous insertion into the heart dictates that the catheter body must be a flexible tube no more than 2 mm in diameter and about 1 meter long. The diameter is constrained by the size of blood vessels used for catheter insertion into the heart. The length is dictated by the length of the catheter inside of the patient's body plus the length of the catheter between the patient and the external equipment.

In the discussion of catheter performance which follows, it is convenient to adopt a cylindrical coordinate system with the z-axis coincident with the catheter axis and pointed toward the distal end. The radial component is in the direction normal to the catheter z-axis, and the circumferential component has a direction around the z-axis. Radius is measured from the catheter axis.

Figure 1A:
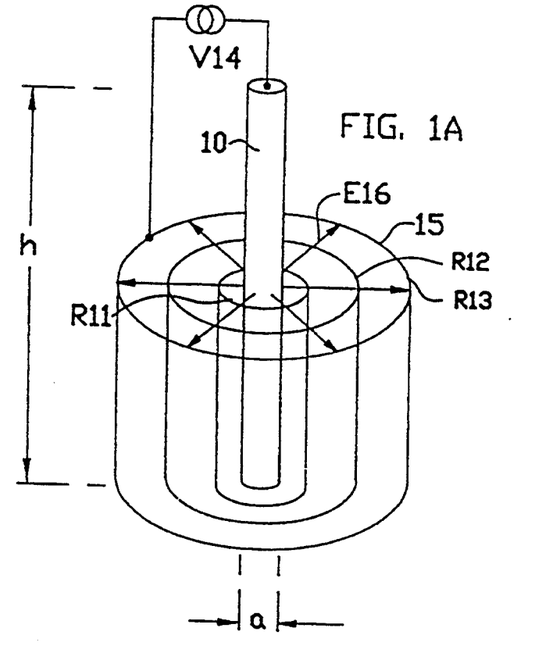
FIG. 1A shows a radial electric field of an antenna represented by a conductor immersed in a lossy dielectric medium.

A simple cylindrical wire heat applicator antenna is shown in FIG. 1A. Applicator antenna 10 is a conductor immersed in a lossy dielectric medium which has electrical properties typical of muscle tissue. The radius of applicator antenna 10 is "a" and its height is "h". In spite of the simple geometry and low frequency approximation used in the description, FIG. 1 retains the salient features of a radial-field coupling of pacing catheters used as an RF antenna.

In FIG. 1A, RF potential V14 is applied in a unipolar manner between applicator antenna 10 and a remote boundary 15 which corresponds to a neutral electrode applied to the skin. The exact location of boundary 15 is not important to the shape of the radial electric field E near applicator antenna 10. Electric field E16 coincides with current density vector $J_r = \sigma E_r$ in the tissue, where $\sigma$ is the conductivity of the tissue.

Continuity of current in the cylindrical geometry in FIG. 1A results in current density $J_r$ which decreases with the inverse of the radius r: $J_r = J_o a/r$ for $r < h$ and power dissipation $P = J_r^2/\sigma = (J_o^2/\sigma)(a/r)^2$. For $r > h$ the spherical geometry is a more appropriate approximation and results in $J_r = J_o(a/r)^2$, and the corresponding electrical power dissipation is $P = J_r^2/\sigma = (J_o^2/\sigma)(a/r)^4$. The result is that the heating of tissue, decreases with the radius within the bounds of the second to the fourth power of a/r. This behavior of the electric field applies to a conducting medium below the microwave region. In the microwave region (f > 900 MHz), the radial attenuation of electric field is even faster due to the "skin depth" attenuation.

Clinical experience indicates that in order to effectively ablate ventricular tachycardia, it is desirable to thermally destroy (ablate) tissue over an area of 1-2 cm$^2$ of the myocardium (e.g., see Moran, J. M., Kehoe, R. F., Loeb, J. M., Lictenthal, P. R., Sanders, J. H. & Michaelis, L. L. "Extended Endocardial Resection for the Treatment of Ventricular Tachycardia and Ventricular Fibrillation", *Ann Thorac Surg* 1982, 34:538–43). As mentioned earlier, in order to accomplish percutaneous insertion into the left ventricle, the heating applicator radius is limited to 1 mm. In order to heat a 2 cm$^2$ area, a 2 cm long applicator can be used provided an effective heating diameter of 1 cm can be reached. To overcome present shortcomings of the RF ablation method, the size of the lesion must be increased and this requires the minimization of the radial attenuation of the electric field and the associated heat dissipation.

The destructive ablation of tissue requires a temperature of approximately 50° C.; this temperature defines the outer radius R of the ablation region. It is therefore desirable to heat tissue to 50° C. up to 5 mm from the catheter axis. Yet at 100° C., undesirable charring and desiccation takes place. So, ideally, the maximum temperature at the applicator electrode boundary should be under 100° C.

Ignoring for a moment heat conduction in the tissue, the rise in tissue temperature is proportional to the electric power dissipation which in turn is proportional to the square of the current density. In order to maintain a 100° C./50° C. or a factor of 2 temperature ratio between the temperature at a radius of 1 mm and the temperature at a radius of 5 mm, the ratio of the power dissipation ratio should be 2 at these two distances. Yet the performance of the current density in FIG. 1A gives at best a power dissipation at the catheter surface of $(R/a)^2$ or 25, and at worse $(R/a)^4$ or 625 times more intense than heat dissipation at a 5 mm radius.

Figure 1B:
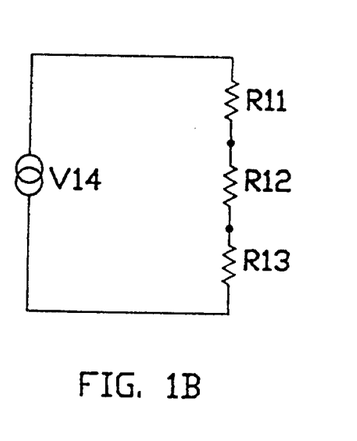
FIG. 1B is an equivalent circuit describing the heat delivery of the radial electric field antenna in FIG. 1A.

In order to examine the effect of this wide range of heat dissipation, it is useful to divide the lossy medium in FIG. 1A into three cylindrical shells: first shell R11 adjacent to the applicator antenna 10, followed by shell R12, and R13 beginning at the 10 mm radius. Since the shells are traversed by the same current, and the potential drop across the shells is additive, power delivery can be schematically represented by three resistances R11, R12, and R13, as shown in FIG. 1B, connected in series with the source of RF potential V14.

The heat required to obtain adequate ablation at a 5 mm radius tends to desiccate blood or tissue close to the applicator antenna 10, increasing the resistivity of R11. This in turn further increases the relative power dissipation in R11 in comparison with R12 and R13, until effective impedance of the desiccated region R11 becomes, in effect, an open circuit shutting off the flow of RF power to the tissue beyond R11.

This indeed is the problem with state-of-the-art RF ablation catheters which severely limits the effective heat delivery to more distant tissue. The currently used RF ablation technique, based on a surgical RF power supply and a pacing catheter, suffers from a steep temperature gradient, reported to decay as $(a/r)^4$ and has the associated problem of charring which disrupts and limits heating and ablation.

Insulation of the applicator antenna 10 from the tissue does not reduce the heat dissipation gradient: If the applicator antenna 10 is insulated from the lossy medium by a thin dielectric tube, the effect of the dielectric can be represented by capacitor (not shown) in series with the source of RF potential V14. Now the applicator must be operated at a frequency high enough so that the impedance of the sum of resistances R11 and R12 and R13 must be higher than the capacitive impedance of the dielectric tube. R11 still dominates the heat distribution.

Effective ablation heating also requires that the heating along the heat applicator axis should be as uniform as possible. Heating should then rapidly attenuate to a negligible value along the portion of the catheter acting as a transmission line.

A key improvement requirement is therefore the ability to ablate areas significantly wider than the catheter diameter, confined only to the region of the heat applicator. Heating should not be limited by charring and desiccation at the catheter boundary.

Therefore, there is a need for a catheter-compatible RF energy delivery system which dissipates heat more uniformly in the radial direction and is well defined in the z direction, thereby leading to a more accurately controlled and larger ablated region. It is also desirable to eliminate the effect of desiccation of tissue, adjacent to the electrode, on heat dissipation to surrounding tissue.

An effective cardiac ablation catheter must satisfy three additional performance requirements:
 (1) The body of the catheter should act as an efficient and reproducible RF power transmission line with the heat applicator transforming the impedance of tissue (electrically a lossy medium) to match the characteristic impedance of the transmission line.
 (2) The detection of an endocardial potential, needed for mapping of location of the arrhythmogenic tissue to be ablated, must coexist, without interference, with the heating function.
 (3) All of the above must be accomplished in a flexible catheter, about 2 mm in diameter so as to allow percutaneous insertion into the left ventricle.

U.S. Pat. No. 4,641,649 issued Feb. 10, 1987 to P. Walinski, A. Rosen, and A. Greenspon describes a cardiac ablation catheter consisting of a miniature coaxial line terminating in a short protruding inner conductor applicator. This system operates at 925 MHz. To applicant's knowledge, no heat dissipation profiles for the Walinski catheter are published. However, the small area of the stub-like applicator results in an E-field attenuation which is even more precipitous than in the case of the pacing catheter electrode discussed in conjunction with FIG. 1A.

Microwave ablation catheter experiments have been reported by K. J. Beckman, & J. C. Lin et al, "Production of Reversible Atrio-Ventricular Block by Microwave Energy" abstracted in *Circulation* 76 (IV): IV-405, 1987. Technical details of a folded dipole applicator catheter used by Beckman have been described by J. C. Lin and Yu-jin Wang in "An Implantable Microwave Antenna for Interstitial Hyperthermia" in *Proceedings of the IEEE*, Vol. 75 (8), p. 1132, August, 1987. The heating profile indicates an unacceptably high heat dissipation along the transmission line. Neither of the two Lin references address the all important issue of integration of monitoring of endocardial potential with the folded dipole heat applicator.

There is a large body of technical knowledge concerned with the RF catheter heating developed for oncological applications. The catheters are inserted typically to the depth of a few centimeters into a cancerous tumor and heat the tumor tissue by a few degrees centigrade. It was found that heated tumor tissue is more susceptible to chemotherapy.

A variety of oncological applicators have been proposed including:

a helix:

(LeVeen, U.S. Pat. Nos. 4,154,246, 22,4,1986; Pchelnikof SU 1,266,548-A-1, Oct. 30, 1986; and Hines et al, U.S. Pat. No. 4,583,556, Apr. 22, 1986);

a helix and a gap: (Stauffer et al, U.S. Pat. No. 4,825,880, Feb. 5, 1989);

linear dipoles:

(B. E. Lyons, R. H. Britt, and J. W. Strohbehn in "Localized Hyperthermia in the Treatment of Malignant Brain Tumors Using an Interstitial Microwave Antenna Array:, *IEEE Trans on Biomedical Engineering* Vol. BME-31 (1), pp. 53–62, January, 1984;

folded dipoles:

(J. C. Lin and Yu-jin Wang "An Implantable Microwave Antenna for Interstitial Hyperthermia" in *Proceedings of the IEEE*, Vol. 75 (8): 1132, August, 1987); and co-linear arrays:

(Kasevich et al, U.S. Pat. Nos. 4,700,716, Oct. 20, 1987).

RF cardiac ablation and oncological applications have the common objective of uniform heating of tissue. There are, however, a number of differences in the requirements for ablation vs. hyperthermia.

Ablation applications require uniform heating, combined with accurate monitoring of the endocardial potential, without interference and preferably without introduction of any additional catheter wires. None of the oncological references quoted above address the issue of monitoring of endocardial potential. Other differences between hyperthermia and ablation are:

(a) Ablation heating must create significantly higher temperature differentials (30° C. for ablation vs. 5° C. for hyperthermia) and must operate in the presence of rapid blood flow, and therefore requires significantly higher power levels. The capabilities of the power supply and the power carrying capability of transmission lines must therefore be higher.

(b) The problem of charring and desiccation, described earlier, is absent in hyperthermia, but it can be a very important obstacle in ablation.

(c) Power leakage on the outside of the catheter transmission line is unimportant in hyperthermia, yet it is unacceptable in cardiac ablation.

(d) Typically in heating of a tumor, an array of antennas is used and so the interaction of the antennas is important. In ablation, only a single element is used so interactive properties are unimportant.

SUMMARY OF THE INVENTION

Accordingly, a principal object of the invention is an RF cardiac ablation catheter, optimized for deep and uniform heat dissipation, and incorporating means for accurate pickup of an endocardial EKG potential in the proximity to the catheter tip. This applicator exhibits deeper and more uniform heat dissipation and is less subject to power reduction from desiccation of tissue in the proximity of the applicator, typical of state-of-the-art devices.

A further object of the invention is a cardiac ablation system which provides monitoring and control of RF power supplied to the catheter and which also provides endocardial signal processing and monitoring, and an electrogram display of the endocardial signal, optimized for convenient mapping of arrhythmogenic tissue.

Yet another object of the invention is an improvement in hyperthermia catheters for application such as hyperthermia treatment of cancer where the catheter with RF energy applicator offers adjustable depth of heating compatible with a tumor size.

Further advantages of the invention will become apparent from the consideration of the drawings and the ensuing description thereof.

DESCRIPTION OF THE PREFERRED EMBODIMENT

FIG. 1A shows a radial electric field (E16) antenna represented by a conductor immersed in a lossy dielectric medium. FIG. 1B is an equivalent circuit of heat delivery of the radial electric field antenna. Both figures have been discussed in the Background of the Invention section above.

Figure 2A:
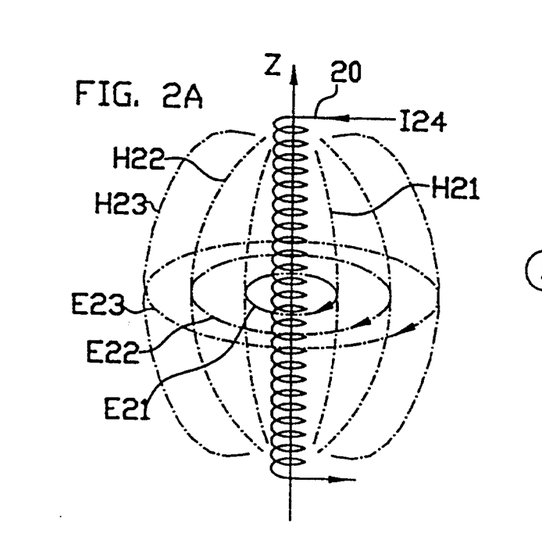
FIG. 2A shows a solenoidal antenna in the form of a helix immersed in a lossy dielectric medium and generating an azimuthal electric field.

FIG. 2 shows a conductor in the form of a helix 20 traversed by RF current I24. The radius of helix 20 in a catheter application is typically a=1 mm and the maximum desired radius of tissue heating for cardiac ablation is R=5 mm.

Generally, a helix can support two modes of operation: transverse electric (TE) and transverse magnetic (TM) mode. In the transverse electric mode (E field transverse to the z-axis), shown in FIG. 2A, the dominant component of the electric field is the azimuthal $E_\theta$ component shown as $E_{21}$, $E_{22}$ and $E_{23}$. The corresponding magnetic field lines $H_{21}$, $H_{22}$, and $H_{23}$ have axial $H_z$ and radial $H_r$ components. In the transverse magnetic mode (not shown), the lines of E and H are interchanged: magnetic field $H_\theta$ circles the axis and the electric field forms arcs with $E_r$ and $E_z$ components. FIG. 1 is a special case of the TM mode showing only the radial component of the electric field.

Figure 2B:
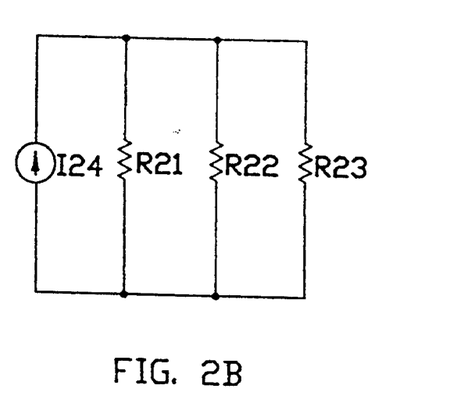
FIG. 2B is an equivalent circuit describing the heat delivery of an azimuthal electric field in FIG. 2A.

The azimuthal electric field $E_\theta$ in the TE mode, and the associated current density $J_\theta = \sigma E_\theta$, is unique in the sense that it does not be begin or end at the catheter surface but in effect circulates around it. In FIG. 2B, the tissue (electrically a lossy medium) is, as in FIG. 1B, divided into three regions: The shell of the lossy medium adjacent to the helix is energized by $E_{21}$, the shell at the intermediate distance energized by $E_{22}$, and the shell corresponding to the boundary of the ablation region is energized by $E_{23}$. The resulting current paths are parallel to each other and so appear in FIG. 2B as parallel resistances R21, R22, and R23 respectively, fed by the current source I24.

Now, if desiccation occurs adjacent to the helix, resistance R21 increases. This reduces power dissipation in R21 and increases power dissipation in resistances R22 and R23. In general then, as power is increased to a point of desiccation at a catheter surface, the heat delivered to a desiccated volume decreases in a TE mode antenna while it increases in a TM antenna. Thus, the azimuthal electric field in a TE mode antenna is much less likely to cause excessive desiccation but even if desiccation occurs, it will not lead to a decrease in power dissipation in more remote tissue.

The TE mode dissipates significant amounts of power in the tissue at 915 MHz or above. The TM mode has the advantage that it is effective even at much lower frequencies. The $E_z$ field in the TM mode has somewhat better radial heating penetration capabilities than the $E_\theta$ field. Since there is no clear advantage between the $E_\theta$ in the TE mode and $E_z$ in the TM mode of operation, the choice depends on the application and both the TE, TM and hybrid mode designs are considered here.

Figures 3, 3A, 3B:
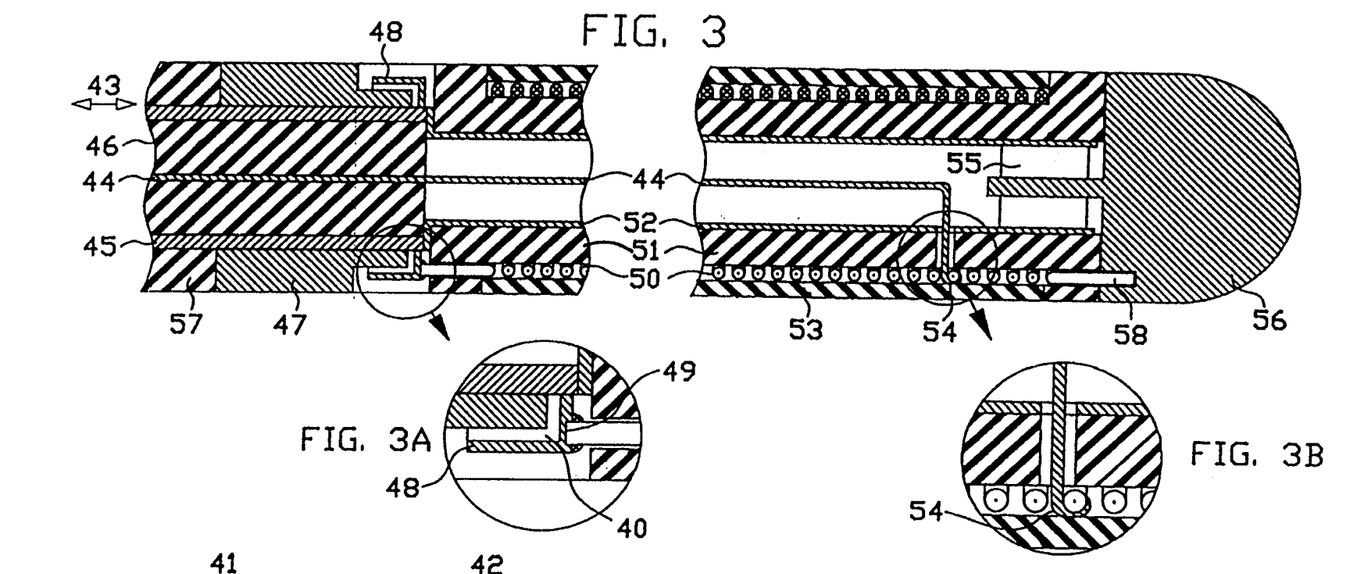
FIG. 3 shows details of a solenoidal antenna mounted on a catheter tip, with endocardial signal monitoring capability.
FIGS. 3A and FIG. 3B show magnified details of FIG. 3.

A solenoidal antenna is defined here as a heating applicator antenna comprising one or more helical windings. One embodiment of the solenoidal antenna in an ablation catheter, with a wire wound helix, is shown in FIG. 3. The antenna in FIG. 3 consists of a helix 50 with three terminals: a proximal end terminal 49 (FIG. 3A), a feed terminal 54 (FIG. 3B), and a distal end terminal 58 (FIG. 3). A heat-shrunk PTFE (also known under trademark TEFLON) plastic sleeve 53 covers the helix 50.

In some applications, it may be desirable to distort the axisymetrical form of the induced E-field. This can be accomplished by partially covering the dielectric sleeve 53 with a metal screen (not shown). Currents induced in the screen will modify the shape of a heating pattern and so serve as an aperture antenna. An asymmetrical field pattern can also be accomplished by a loop antenna, e.g., located in the r-z plane.

A transmission line which connects the distal end of the catheter to external equipment has the form of a coaxial line 43 shown in FIG. 3. In a preferred embodiment, coaxial line 43 includes a center conductor 44 (approximately 0.16 mm diameter), a dielectric 46 (approximately 1.35 mm outside diameter), a metal braid shield 45 and an insulating sleeve 57 (approximately 1.8 mm outside diameter). A small diameter and flexible construction make the coaxial line 43 suitable for biomedical catheter applications.

A distal monitoring electrode 56 is connected to a distal end terminal 58 of helix 50 and to bypass capacitor 55. Bypass capacitor 55 is connected to shield 45 through metallized coating 52 inside of core 51. The function of the bypass capacitor 55 is to ground RF power. Thus when the RF power is applied to the helix 50, distal monitoring electrode 56 has little RF voltage thereby preventing distal monitoring electrode 56 from acting as a heat applicator. Distal monitoring electrode 56, in conjunction with a proximal monitoring electrode 47, picks up an endocardial potential. In this embodiment, the distance from a beginning of proximal monitoring electrode 47 to an end of the distal electrode 56 is approximately 20 mm.

When operated in a TE mode the number of turns of helix 50 is chosen so that at an operating frequency of 915 MHz, the helix is somewhat short of being at a quarter wavelength resonance. Helix 50 is wound on a dielectric core 51. The proximal end terminal 49 of helix 50 is connected to a variable tuning capacitor 48 (FIG. 3A). Variable tuning capacitor 48 is moved with respect to proximal monitoring electrode 47 during manufacture for tuning to a resonance at operating conditions. Tuning capacitor 48 is controlled by adjusting a space 40 between capacitor electrodes 47 and 48. At lower frequencies, the capacitance of inter-electrode space is insufficient and the capacitor is implemented by a discrete component.

RF power is coupled to a helical resonator by connecting the center conductor 44 to helix 50 at the feed terminal 54 (see FIG. 3B). The position of feed terminal 54 on the helix is selected for a good match between the characteristic impedance of the coaxial line 43 and the impedance of the resonator under typical operating conditions. Under some circumstances the best match can be obtained when the feed terminal 54 and the distal end terminal 58 coincide, and the helix 50 is fed at its distal end terminal. The choice of an axial quarter wavelength resonator is by no means unique. One could just as well select any multiplicity of quarter wavelengths, such as a half-wavelength resonator.

When in operation in the TM mode, the frequency of operation can be much lower, e.g., 27 MHz. Helix 50 can then be viewed as a discrete inductance, tuned into series resonance by a discrete component capacitor 48. In the TM mode, core 51 on which helix 50 is wound, can be made from a ferrite. At 27 MHz, a ferrite core can significantly increase inductance of the helix and decrease losses in the tuned circuit. In order to use the $E_z$ electric field component in the TM mode, sleeve 53 is removed to allow direct contact between the winding of the helix and the surrounding tissue.

Figure 4:
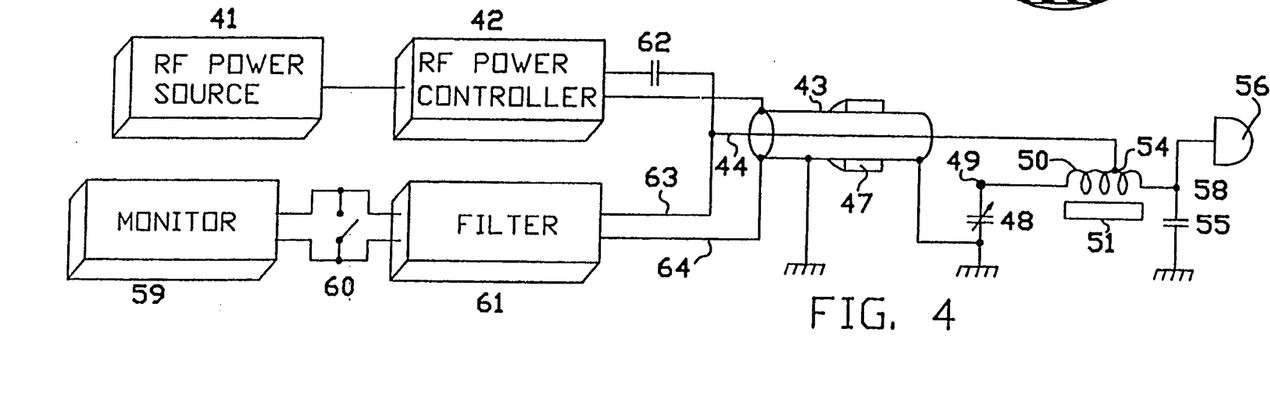
FIG. 4 is a block diagram of an RF heating and intracardiac electrogram monitoring catheter ablation system.

In cardiac ablation, it is essential to be able to monitor endocardial potential just before and after the application of heat. Before application of heat, it is necessary to locate the arrhythmogenic tissue to be ablated. Afterward, endocardial potential is used to assess effectiveness of destruction of arrhythmia-causing myocardial tissue. FIG. 4 shows a block diagram of a system which combines controlled heat delivery by a solenoidal antenna, with monitoring of endocardial potential.

Distal monitoring electrode 56, in conjunction with the proximal monitoring electrode 47, picks up a local endocardial potential and feeds this signal through coaxial line 43 to capacitor 62. Capacitor 62 represents a short circuit for the RF power and an open circuit for a much lower frequency band (typically 0.1 Hz to 100 Hz) associated with endocardial signals. An endocardial signal travels unobstructed on lines 63 and 64 to an input to a low-pass filter 61.

Low-pass filter 61 has a high input impedance to the RF power and therefore blocks the transmission of RF power to switch 60 while allowing passage of the endocardial signal. Switch 60 is closed simultaneously with application of RF power, thus providing additional protection for monitor 59. Intracardiac signal processing, display, and recording is accomplished by monitor 59 which displays the intracardiac electrogram. Existing equipment is suitable for application as monitor 59.

RF power is generated in an RF power source 41. The RF power is controlled and monitored in controller 42 which couples the RF power to the coaxial line 43 through capacitor 62, which for RF represents substantially a short circuit.

Figure 5:
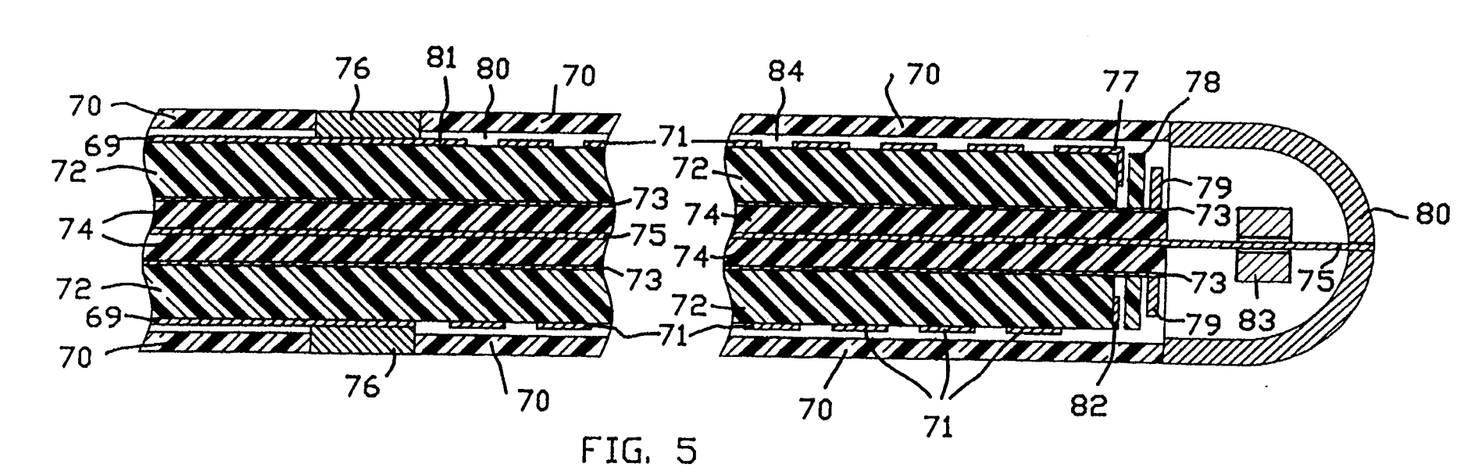
FIG. 5 shows a tri-axial catheter constructed from plated plastic.

FIG. 5 shows an alternative implementation of a catheter using metal plating on plastic, such as silver on PTFE. Such plating offers a number of advantages over the design shown in FIG. 3. One advantage is a unitary design: the plating process can in one step create coaxial shield 69, helix 71, and disk 82 serving as a capacitive coupling electrode. In microwave application, shield 69 may be used alone or in conjunction with a secondary shield made from a metal braid (not shown).

Another advantage is that helix 71 made from a metal strip provides a more effective use of the metal cross-section than the circular cross-section wire such as used in the helix 50 in FIG. 3. For silver or copper, the RF current penetrates only 0.01 mm at 27 MHz and 0.002 mm at microwave frequencies. This so called "skin depth" is so small in good conductors that plating thickness easily exceeds it. In round wires, the current flows only on the surface, yet the wire adds two diameters to the diameter of the catheter, without any contribution to conduction.

FIG. 5 shows a tri-axial design of the catheter. A coaxial RF transmission line is formed between coaxial shield 69, plated on the outside of the plastic tube 72, and an inner conductor 73 plated on the outside of a smaller plastic tube 74. A stranded small-gauge center wire 75, along the axis of plastic tube 74, is shielded from the RF by plated inner conductor 73. Center wire 75 is used to transmit endocardial signals from distal monitoring electrode 80. Optionally a ferrite bead 83 acts as a RF choke to further decouple RF from distal monitoring electrode 80. A proximal monitoring electrode 76, in the form of a ring, is seated on and makes electrical contact with the shield 69.

A proximal end terminal 81 of the plated helix 71 seamlessly joins with the shield 69. A distal end terminal 77 of the helix 71 seamlessly joins with plated disk 82, plated on an end surface of plastic tube 72. Metal disk 79 connects along its inside diameter to inner conductor 73. Dielectric disk 78 separates the metal disk 79 from the plated disk 82. The three discs 82, 78 and 79 form a capacitor between inner conductor 73 and the helix 71. The role of this capacitor is to tune the inductance of the helix 71 to resonance so that under operating conditions, the transmission line sees a resistive load equal to a characteristic impedance of the coaxial line.

A capacitance between the turns of the helix 71 in the plated strip design is much smaller than a comparably spaced circular cross-section wire. It is therefore possible to make the gap 84 between turns significantly smaller in a plated strip design. This narrow-gap geometry generates an intense electric field between turns, primarily z-axis oriented across the gap, with a rather steep attenuation in the radial direction. As a result, most of the $E_z$ field passes through the dielectric cover tube 70 without penetrating into the outside tissue. The dominant component of the electric field in the tissue is the azimuthal field $E_\Theta$ induced by current in helix 71. The advantages of the $E_\Theta$ field have been discussed earlier.

Figure 6:
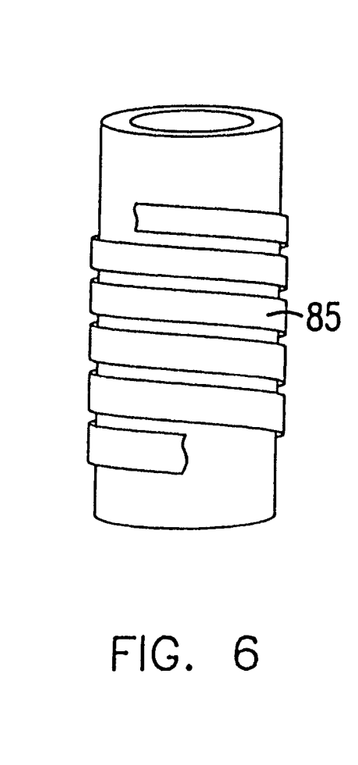
FIG. 6 shows an embodiment of the invention utilizing a helix having a variable strip width.
Figure 7:
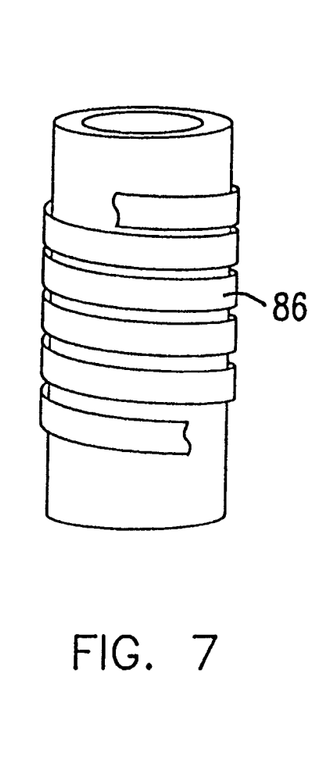
FIG. 7 shows an embodiment of the invention utilizing a variable gap helix.

Yet another advantage of metal-on-plastic plating is that a variety of antenna patterns can be readily and accurately implemented. For example, a helical strip 85 in FIG. 6 has a variable width constant-gap winding. A helical strip 86 in FIG. 7 has a constant width variable-gap winding. This type of helical strip (85 or 86) design allows control of the electric field distribution in the z-direction.

Figure 8:
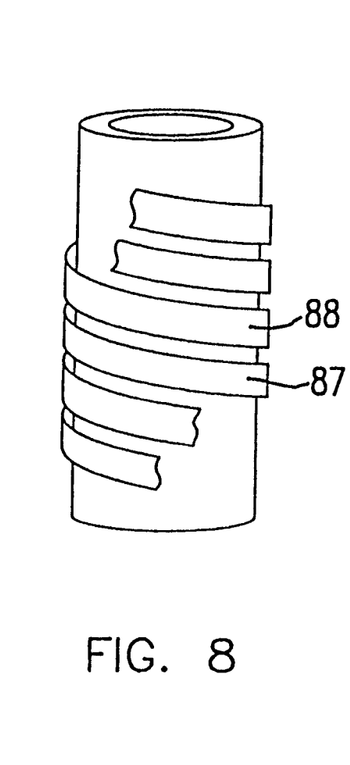
FIG. 8 shows an embodiment of the invention utilizing a bifilar helical antenna.

An antenna in FIG. 8 consists of two interspaced helices 87 and 88, wound in the same sense and defining a bifilar antenna geometry. The bifilar helices have two proximal end terminals and two distal terminals. The proximal end terminals can be connected to the transmission line and the distal end terminals can be shorted or preloaded with an RF impedance to optimize the power flow.

Figure 9:
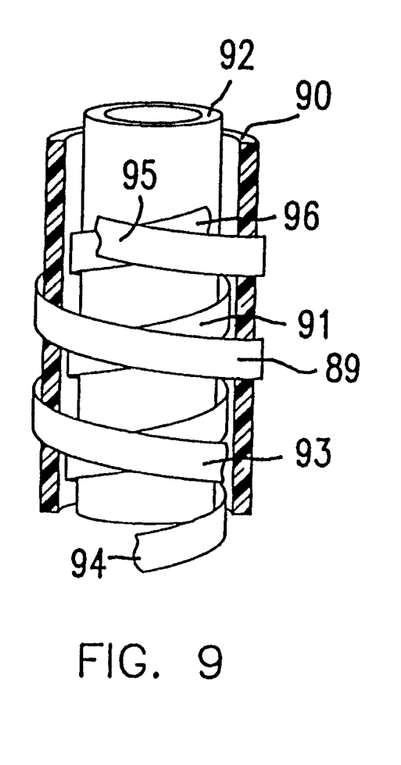
FIG. 9 shows an embodiment of the invention utilizing a cross-wound helical antenna.

An antenna in FIG. 9 consists of a helix 89, plated on a plastic sleeve 90 (shown partially cut), and helix 91 plated on a plastic tube 92. The two helices 89 and 91 are wound in an opposite sense and therefore cross over each other, defining a cross-wound antenna geometry. Like the bifilar antenna, a cross-wound antenna has two proximal end terminals 93 and 94 and two distal end terminals 95 and 96. The proximal end terminals can be connected to a transmission line and the distal end terminal can be shorted or preloaded with an RF impedance to optimize the power flow. It should be noted that in this configuration, unlike the bifilar configuration of FIG. 8, current entering at proximal end terminal 93 and flowing up through helix 89 circulates around the axis in the same direction as the current flowing down through helix 91 and exiting at proximal terminal 94. An effect on induced azimuthal fields $E_\Theta$ is therefore additive. The polarity of the $E_z$ field caused by the up current in helix 89 and the down current in helix 91 is opposite, and thus tends to cancel each other. The cross-wound antenna is therefore an efficient source of the azimuthal $E_\Theta$ field.

Figure 10:
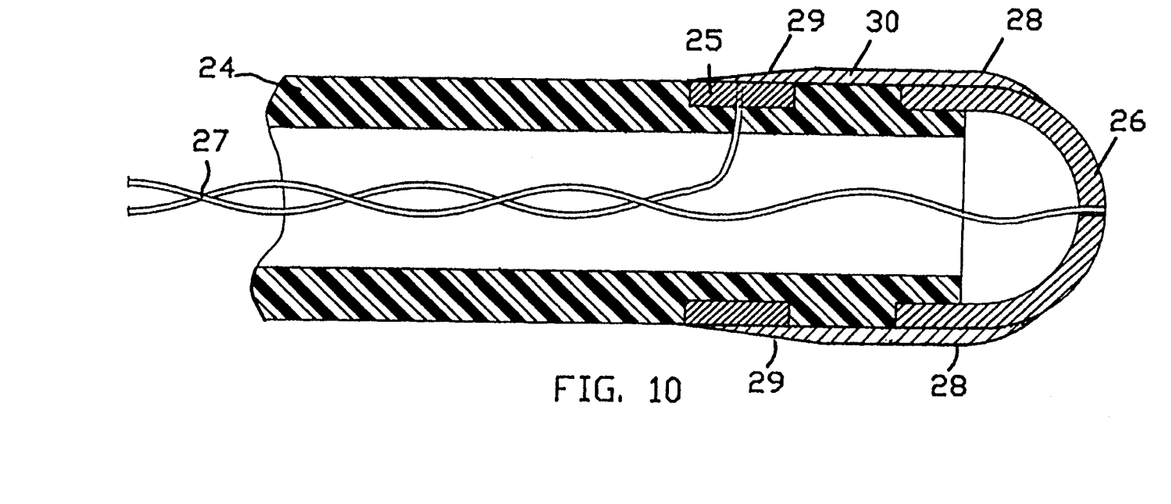
FIG. 10 shows an embodiment of the invention utilizing a variable surface impedance catheter antenna.

All of the antennas described thus far are of the solenoidal variety, i.e., include one or more helices. The antenna shown in FIG. 10 is different. FIG. 10 shows a proximal ring electrode 25 and a distal tip electrode 26, mounted or plated on a catheter tube 24 and shaped very similarly to the currently used pacing catheters. An electrical connection is maintained by a twisted pair transmission line 27. Unlike currently used catheters where the electrodes are made from plain metal, proximal ring electrode 25 and distal tip electrode 26 have their metallic surface coated with control coatings 28 and 29 respectively. Optionally, the gap between proximal ring electrode 25 and distal tip electrode 26 can be filled with gap coating 30. (Thickness of coatings is exaggerated in FIG. 10 for the sake of clarity.)

The control coatings vary in thickness as a function of the axial distance from the inter-electrode gap, being thickest along the edges of the inter-electrode gap and thinning away from the gap. Without the coating, the strongest $E_z$ field is adjacent to the inter-electrode gap. The coatings, by changing the surface impedance, equalizes the external electric field and improve radial penetration of the field.

The coatings 28, 29, and 30 can be made from a resistive material or from a dielectric. A resistive coating, introduces the highest resistance close to the inter-electrode gap. As a result, the external field adjacent to inter-electrode gap is reduced, the external field intensity is equalized and the radial penetration is improved. A capacitive coating, made from a dielectric, exhibits a smallest capacitive impedance near the inter-electrode gap and accomplishes field equalization similar to the resistive coating. There is, however, significantly less heat dissipation in the capacitive coating than in the resistive coating.

While certain specific embodiments of improved electrical catheters and systems have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A catheter for thermally destroying myocardial tissue in a heart chamber to treat arrythmia comprising
   a catheter body that carries an antenna having an axis,
   means for conducting electromagnetic power to the antenna while the catheter body is immersed in blood in a heart chamber, and
   means for conditioning the antenna to emit a helically generated electromagnetic field about the antenna axis that penetrates, heats, and thermally destroys myocardial tissue beyond the catheter body.

2. A catheter for thermally destroying myocardial tissue in a heart chamber to treat arrythmia comprising
   a catheter body that carries a solenoidal antenna having an axis,
   means for conducting electromagnetic power to the solenoidal antenna while the catheter body is immersed in blood in a heart chamber, and
   means for conditioning the solenoidal antenna to emit an electromagnetic field about the antenna axis to penetrate, heat, and thermally destroy myocardial tissue beyond the catheter body.

3. A catheter according to claim 1
   and further including means carried by the catheter body for monitoring an endocardial signal.

4. A catheter according to claim 2
   wherein the antenna is conditioned to emit the electromagnetic field symmetrically about the axis of the antenna.

5. A catheter according to claim 2
   wherein the antenna is conditioned to emit the electromagnetic field asymmetrically about the axis of the antenna.

6. A cardiac ablation catheter comprising
   a catheter body,
   solenoidal antenna means having an axis and carried within the catheter body, the solenoidal antenna means being operative, when conducting electromagnetic power, for emitting an electrical field while the catheter body is immersed in an intra-cardiac medium to thereby heat tissue, and
   power transmission means for connecting the solenoidal antenna means to an external source of electromagnetic power comprising a conductive connection at a first point of the solenoidal antenna means and a capacitive connection at a second point of the solenoidal antenna means to selectively condition the solenoidal antenna means, based upon the frequency of the conducted electromagnetic power, to operate in a first mode for heating tissue beyond the catheter body by emitting a helically generated electrical field that circulates around the catheter body in radially spaced arcuate paths about the solenoidal antenna means axis; to alternatively condition the solenoidal antenna means to operate in a second mode for heating tissue by emitting an electrical field that extends radially from the solenoidal antenna means axis; and to alternatively condition the solenoidal antenna means to operate in a range of modes between the first and second modes.

7. A catheter according to claim 6
   and further including electrode means carried by the catheter body for monitoring an endocardial signal.

8. A catheter according to claim 6
   wherein the power transmission means includes means for altering the capacitive impedance of the capacitive connection.

9. A catheter according to claim 6
   wherein the transmission means includes a fixed capacitive impedance at the capacitive connection.

10. A catheter according to claim 6
    wherein the solenoidal antenna means forms a helix.

11. A catheter according to claim 6
    wherein the helically generated electrical field is symmetric about the axis of the solenoidal antenna means.

12. A catheter according to claim 6
    wherein the helically generated electrical field is asymmetric about the axis of the solenoidal antenna means.

* * * * *

UNITED STATES PATENT AND TRADEMARK OFFICE
CERTIFICATE OF CORRECTION

PATENT NO. : 5,370,644

DATED : December 6, 1994

INVENTOR(S) : Edwin Langberg

It is certified that error appears in the above-identified patent and that said Letters Patent is hereby corrected as shown below:

Column 11, Claim 3, Line 44: After claim: delete 1 and insert 2.

Signed and Sealed this

Second Day of May, 1995

Attest:

BRUCE LEHMAN

Attesting Officer

Commissioner of Patents and Trademarks